(12) United States Patent
Ito (10) Patent No.: US 7,081,228 B1
(45) Date of Patent: Jul. 25, 2006

(54) APPARATUS FOR PREPARING A FLUID SAMPLE ALIQUOT

(75) Inventor: Ralph K. Ito, Hopkinton, MA (US)

(73) Assignee: Olympus America Inc., Melville, NY (US)

( * ) Notice: Subject to any disclaimer, the term of this patent is extended or adjusted under 35 U.S.C. 154(b) by 660 days.

(21) Appl. No.: 09/400,034

(22) Filed: Sep. 21, 1999

(51) Int. Cl.
*B01L 3/02* (2006.01)

(52) U.S. Cl. ...................... 422/100; 422/103

(58) Field of Classification Search ............... 422/100, 422/103; 222/95, 214, 571, 562, 544; 73/864.01
See application file for complete search history.

(56) References Cited

U.S. PATENT DOCUMENTS

| | | | |
|---|---|---|---|
| 2,083,603 A * | 6/1937 | Hardwick | 222/95 |
| 4,037,464 A | 7/1977 | Wenander | 73/61.4 |
| 4,195,526 A | 4/1980 | Amos et al. | 73/425.6 |
| 4,249,419 A | 2/1981 | Thomas | 73/425.6 |
| 4,298,575 A | 11/1981 | Berglund | 73/864.13 |
| 4,369,664 A | 1/1983 | Bunce et al. | 73/864.12 |
| RE31,555 E | 4/1984 | Garren et al. | 73/864.11 |
| 4,459,267 A | 7/1984 | Bunce et al. | 422/100 |
| 4,483,825 A | 11/1984 | Fatches | 422/100 |
| 4,707,337 A * | 11/1987 | Jeffs et al. | 422/100 |
| 4,740,472 A | 4/1988 | Burtis et al. | 436/63 |
| 4,830,226 A | 5/1989 | Kong | 222/205 |
| 4,967,606 A | 11/1990 | Wells et al. | 73/864.18 |
| 5,090,255 A | 2/1992 | Kenney | 73/1 |
| 5,096,093 A | 3/1992 | Wells | 222/95 |
| 5,182,082 A | 1/1993 | Monthony et al. | 422/57 |
| 5,322,192 A | 6/1994 | Godolphin et al. | 222/83 |
| 5,399,316 A | 3/1995 | Yamada | 422/58 |
| 5,406,856 A | 4/1995 | Kuhn | 73/864.14 |
| 5,510,083 A | 4/1996 | Sack et al. | 422/100 |
| 5,681,742 A | 10/1997 | MersKelly et al. | 435/288.1 |
| 5,814,276 A | 9/1998 | Riggs | 422/65 |
| 6,432,366 B1 * | 8/2002 | Ruediger et al. | 422/100 |

* cited by examiner

*Primary Examiner*—Matthew O. Savage
(74) *Attorney, Agent, or Firm*—Straub & Pokotylo; John C. Pokotylo (57) ABSTRACT

A sample aliquot pipette tip (SAT) includes a pipette tip and a sample aliquot cup. The pipette tip is collapsible. The sample aliquot cup is arranged above the pipette tip and is fluidly coupled with the pipette tip. The SAT works in concert with a tip aliquot support (TAS). The TAS may include a channel for accepting a collapsed pipette tip of an SAT, a support for accommodating a sample aliquot cup of a SAT and a constricted passage arranged between the support and the channel. As an SAT is inserted into a TAS, the constricted passage of the TAS collapses the pipette tip of the SAT. The collapsed pipette tip of the SAT is then received by the channel of the TAS. When the SAT is fully inserted into the TAS, the support of the TAS accommodates the sample aliquot cup of the SAT.

26 Claims, 6 Drawing Sheets

APPARATUS FOR PREPARING A FLUID SAMPLE ALIQUOT

§ 1. BACKGROUND OF THE INVENTION

§ 1.1 Field of the Invention

The present invention concerns automating laboratory procedures and, in particular, concerns methods and apparatus for preparing a fluid sample aliquot. The present invention also concerns a system for preparing and managing fluid sample aliquots using such methods and apparatus.

§ 1.2 Related Art

Laboratory procedures are often used to manage fluid samples. For example, in a laboratory process, a blood sample may be used for diagnostic purposes. Similarly, fluid samples may be used in combinatorial chemistry to create different chemical compounds. In this context, the term "aliquot" refers to a precisely measured quantity, such as a quantity of a fluid for example. The aliquot may be drawn from a larger fluid sample using a pipette. In the context of the present invention, a liquid sample should have a minimum amount (or, alternatively, a precise amount) needed to perform a particular test. Thus, the term "aliquot", as used herein, should be interpreted broadly. A pipette is a tube, typically glass or plastic, which is open at both ends and which is used to transfer small volumes of fluid. In the past, such procedures were performed manually. More recently, however, clinical laboratories have become increasingly automated to reduce labor costs.

Some known automatic pipetting systems may move a pipette up and down, and radially and/or laterally. Such automatic pipetting systems may use disposable plastic pipette tips to prepare an aliquot as follows. First, a plastic pipette tip is friction fit onto a nipple of the system, for example, via a pressing operation. Then, the pipette tip is located over a fluid sample source, such as a test tube for example. The pipette tip is then lowered into the fluid sample and an aliquot is drawn, using suction for example. The pipette tip is then raised and positioned over a destination container, such as another test tube or cuvette for example, into which the aliquot is dispensed. The pipette tip is then relocated and discarded (that is, removed from the nipple of the automatic pipetting system).

Unfortunately, this known system has some inefficiencies, both in its economy of motion and in the materials that it uses. Thus, an improved pipetting system, as well as improved components for use in such an improved system, are needed.

Other known laboratory automation systems integrate stations and components from a single manufacturer. Unfortunately, this limits flexibility, both in the budget and configuration of the system. Thus, an automated laboratory should be able to use components and stations from a number of different vendors, thereby permitting the best and/or most cost-effective components to be used.

§ 2. SUMMARY OF THE INVENTION

The present invention discloses a sample aliquot pipette tip (also referred to as a "SAT") which includes a pipette tip and a sample aliquot cup. The pipette tip is used for drawing a fluid sample from a source. The pipette tip is formed to be collapsible and may be plastic, for example. The sample aliquot cup is arranged above the pipette tip and is fluidly coupled with the pipette tip. The size of the sample aliquot cup is designed to hold the desired aliquot volume.

The present invention also discloses a tip aliquot support (also referred to as a "TAS"). The TAS may include a channel for accepting a collapsed pipette tip of a SAT, a support for accommodating a sample aliquot cup of a SAT and a constricted passage arranged between the support and the channel. As a SAT is inserted into a TAS, the constricted passage of the TAS collapses the pipette tip of the SAT. The collapsed pipette tip of the SAT is then received by the channel of the TAS. When the SAT is fully inserted into the TAS, the support of the TAS accommodates the sample aliquot cup of the SAT.

The present invention also discloses a method for using the SAT and TAS. The method may include steps of inserting a SAT having a fluid sample in its pipette tip into a TAS. During such an insertion, the constricted passage of the TAS will force the fluid sample in the pipette tip of the SAT upward, until it is contained in the sample aliquot cup of the SAT.

The present invention also discloses an automated aliquot preparation system which uses the SAT-TAS combination for pipetting, labeling, and transporting fluid samples. The automated aliquot preparation system may include a conveyer for transporting a liquid sample source, a bar code reader for scanning a bar code of the liquid sample source, a gate for selectively diverting the liquid sample source based on its bar code, a printer for duplicating the bar code onto a sample aliquot cup portion of a SAT, and an automated pipetting system for positioning the pipette tip of the SAT within the fluid sample source, for drawing a sample from the fluid sample source into the pipette tip of the SAT, and for inserting the SAT into an empty TAS. One or more TASes may be held in a rack.

§ 3. BRIEF DESCRIPTION OF THE DRAWINGS

FIG. 8A is a side-plan perspective view.

§ 4. DETAILED DESCRIPTION

In the following, SAT-TAS combinations will first be described in § 4.1. Then, an automated aliquot preparation system, which uses the SAT-TAS combination, will be described in § 4.2.

§ 4.1 SAT-TAS Combination

This section describes SAT-TAS combinations. First, functions which may be performed by a SAT-TAS combination are introduced in § 4.1.1 below. Then, exemplary structures of a SAT and of a TAS are described in § 4.1.2 below. Finally, an operation of an exemplary SAT-TAS combination is described in § 4.1.3 below.

§ 4.1.1 Functions of a SAT-TAS Combination

Basically, the SAT-TAS combination functions to prepare an aliquot of a sample liquid. The SAT functions to interface with an automated pipetting system. Together with the automated pipetting system, the SAT also functions to draw a fluid sample from a fluid sample source. The TAS functions to force the fluid sample from a pipette tip of the SAT into a sample aliquot cup of the SAT. Thus, the SAT also functions as a sample cup when inserted into a TAS. The TAS also functions to hold a SAT inserted therein.

§ 4.1.2 Exemplarly Structures of a SAT and TAS

Figure 1:
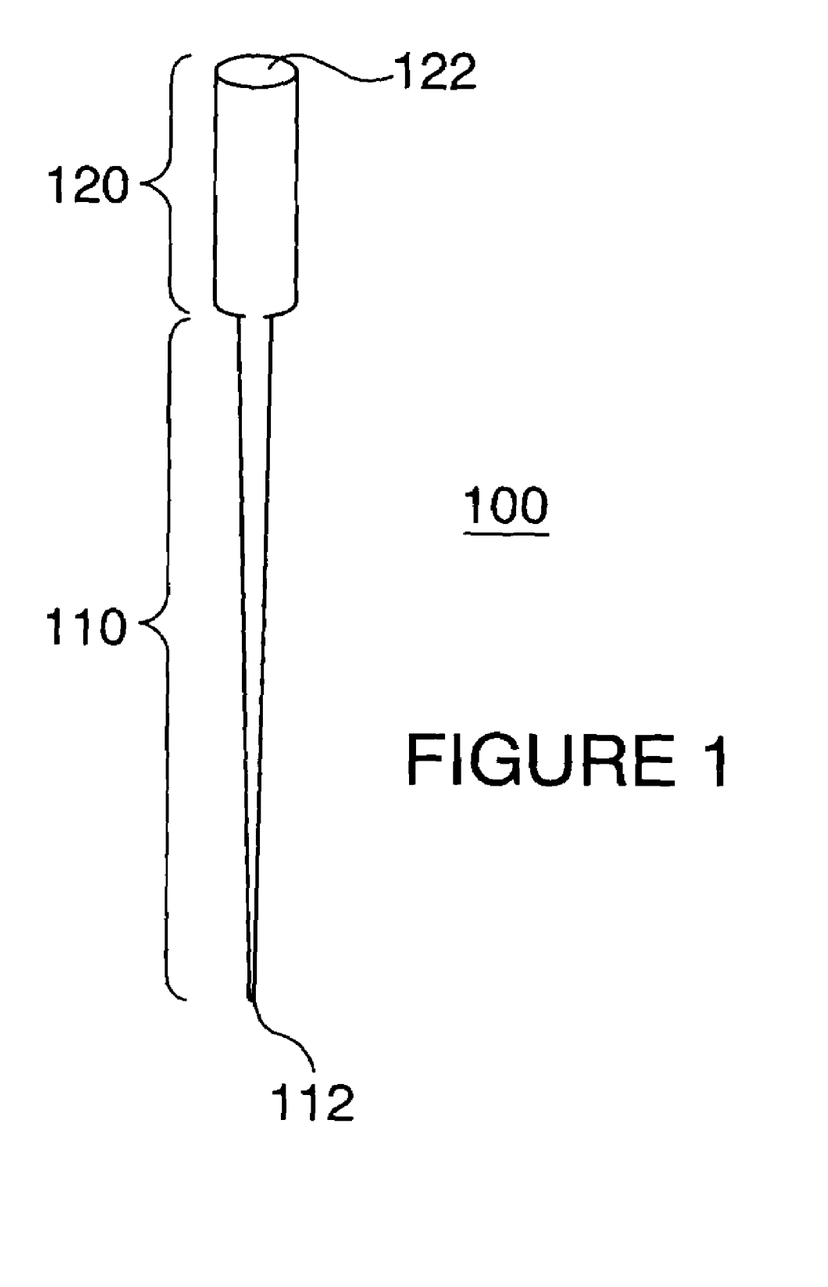
FIG. 1 is a side-plan perspective view of a sample aliquot pipette tip (or "SAT").

FIG. 1 is a side-plan perspective view of a sample aliquot pipette tip (or "SAT") 100. The SAT 100 includes a pipette tip section 110 and a sample aliquot cup section 120. The pipette tip 110 is used for drawing, through an open end 112 at its tip, a liquid sample from a source. In one embodiment, the pipette tip 110 may be approximately 10 to 11 cm long and may have a volume of approximately 3 ml. The pipette tip 110 is formed to be flexible and collapsible. For example, the pipette tip 110 may be a plastic, such as polyvinyl chloride (or "PVC") or polypropelyne. The walls forming the pipette tip 110 are designed such that they do not crack when squeezed together and such that they can form a liquid seal when squeezed together. The sample aliquot cup 120 is arranged above, and is fluidly coupled with, the pipette tip 110. The sample aliquot cup 120 includes an open end 122 which may be engaged, for example via a friction fit or via suction, by pipetting means. Thus, the open end 122 may be dimensioned to mate with an automated pipetting system. The size of the sample aliquot cup 120 may be selected to hold the desired aliquot volume. In one embodiment, the sample aliquot cup 120 is approximately 3 to 4 cm long and has a diameter of approximately 12 to 13 mm.

Figure 2:
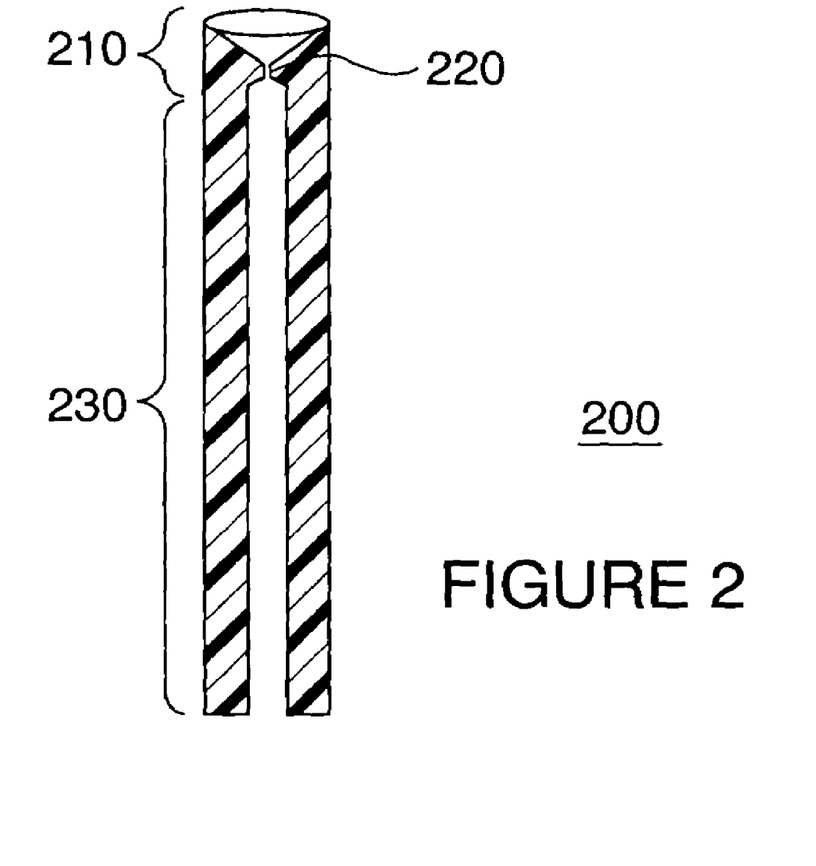
FIG. 2 is a side-plan perspective view of a tip aliquot support (or "TAS").
Figure 3:
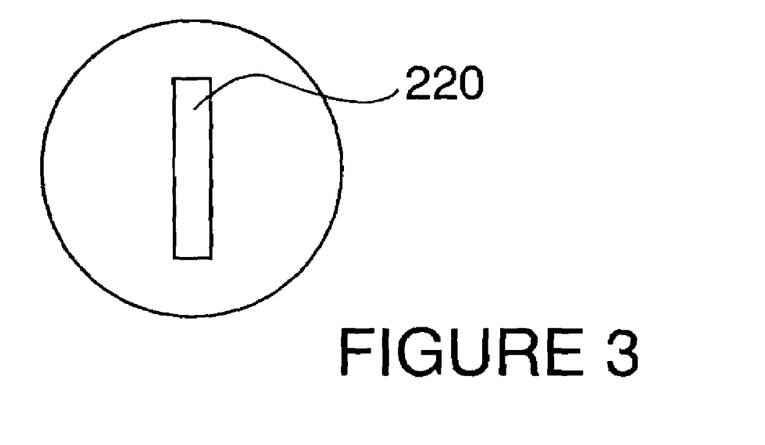
FIG. 3 is a plan view of the TAS of FIG. 2.

FIG. 2 is a side-plan perspective view of a tip aliquot support (or "TAS") 200. The TAS 200 may include a channel or cavity 230 for accepting a collapsed pipette tip 110 of a SAT 100, a support 210 for accommodating a sample aliquot cup 120 of a SAT 100, or at least a bottom portion of a sample aliquot cup of a SAT 100, and a constricted passage 220 arranged between and connecting the support 210 and the channel 230. Notice that the support 210 has a funnel shape. In an alternative embodiment, the support 210 may be tapered in general. In any event, the shape of the support should match at least the bottom portion of the sample cup 120 of the SAT 100. FIG. 3 is a plan view of the TAS 200 of FIG. 2 which illustrates an exemplary constricted passage 220. In this example, the constricted passage is a rectangular slot. Naturally, the cross-section of the constricted passage 220 may have other shapes, such as racetrack, elliptical, circular, square, etc. However, the constricted passage 220 should be shaped and dimensioned such that, when the pipette tip 110 of a mating SAT 100 is inserted through it, the pipette tip 110 is completely collapsed against itself such that any and all liquid in the pipette tip 110 is forced upward, above the constricted passage 220, by the constricted passage 220.

Figure 4A:
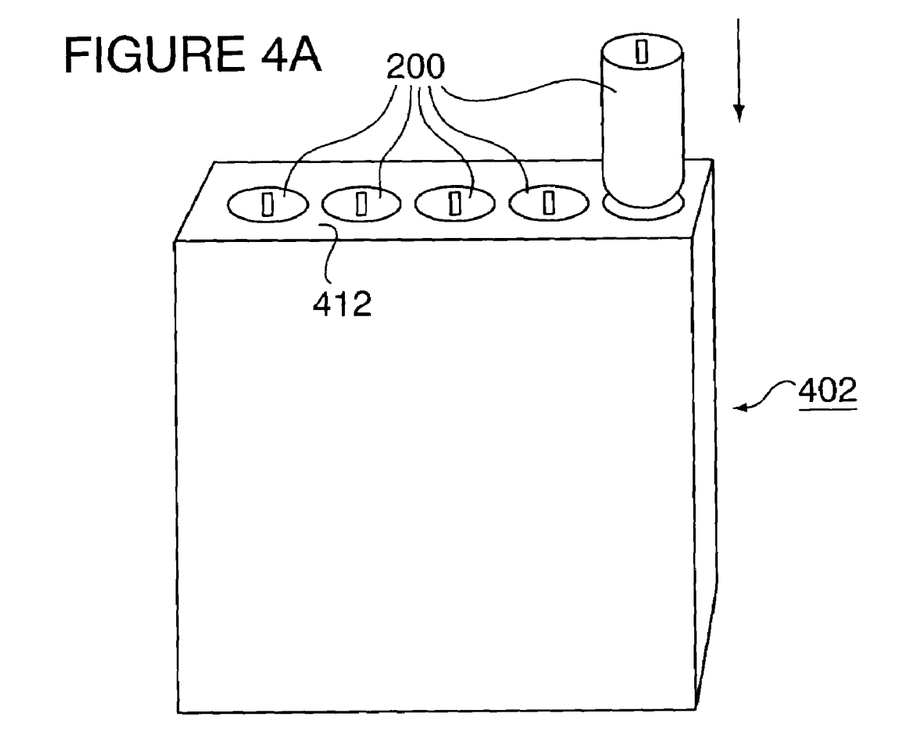
FIG. 4*a* is a side-plan perspective view of a TAS being inserted into a TAS holder.

FIG. 4a is a side-plan perspective view of a TAS 200 being inserted into a first exemplary TAS holder 402 which is already holding four (4) other TASes 200. Notice that this TAS holder 402 can accommodate up to five (5) TASes 200. Notice also that, when inserted, the top of a TAS 200 is substantially flush with a top surface 412 of the TAS holder 402.

Figure 4B:
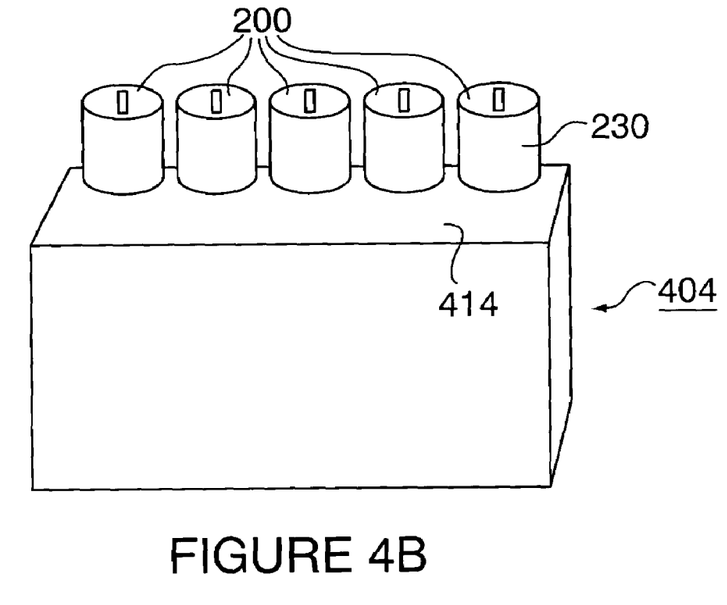
FIG. 4*b* is a side-plan perspective view of a plurality of TASes accommodated in an alternative TAS holder.

FIG. 4b is a side-plan perspective view of an alternative TAS holder 404, such as a five-position personality rack from Hitachi, Ltd. of Tokyo, Japan, for example, which accommodates five (5) TASes 200. In this alternative TAS holder 404, when inserted, a top portion 230 of a TAS 200 extends beyond the top surface 414 of the TAS holder 404. Basically TASes 200 can be inserted into any "personality rack", such as a five-position personality rack from Hitachi, Ltd. of Tokyo, Japan, a ten-position personality rack from Olympus Optical Co., Ltd. of Tokyo, Japan, or a DPC immunoassay rack.

Figure 7:
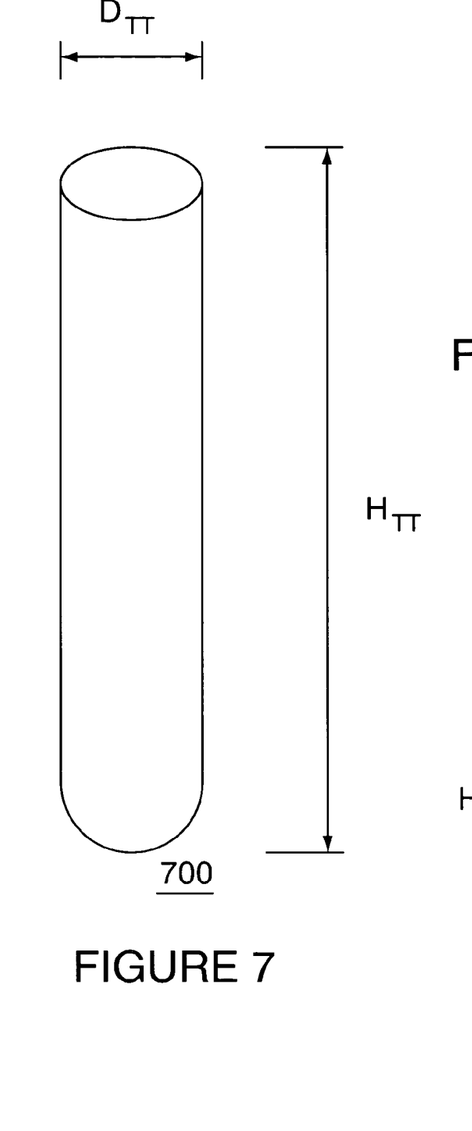
FIG. 7 is a side-plan perspective view of a test tube.
Figure 8A:
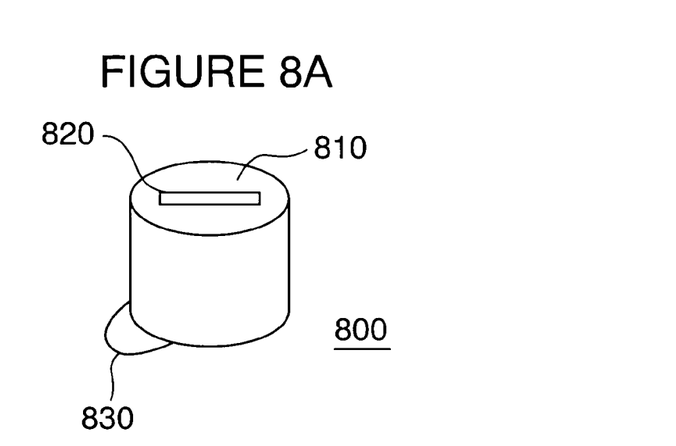
Figure 8B:
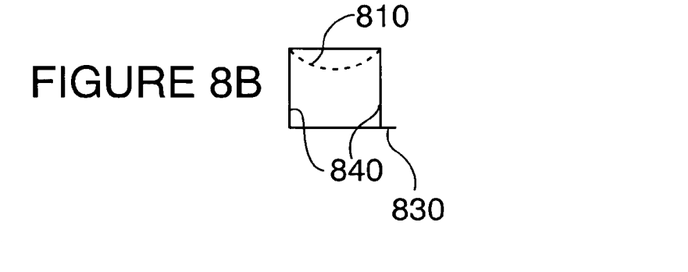
FIG. 8B is a side view, of a cap which, when combined with the test tube of FIG. 7, forms an alternative TAS.

FIGS. 7 and 8A are perspective views of a test tube 700 and a cap 800, respectively, which together can be used to form an alternative TAS. More specifically, the test tube 700 of FIG. 7 has a height of $H_{TT}$ and a diameter of $D_{TT}$. The height $H_{TT}$ of the test tube 700 may be 75 mm, or approximately 75 mm, for example. The diameter $D_{TT}$ of the test tube 700 may be 12 to 13 mm, or approximately 12 to 13 mm, for example. The cap 800 shown in FIGS. 8A and 8B has a cylindrical inner wall 840 which fits snuggly on the outside surface of the test tube 700. Preferably, the inner wall 840 of the cap 800 and the outside surface of the test tube 700 form a fluid-tight seal. The cap 800 includes a funnel-shaped, or concave, top surface 810. A slot 820 is defined through the top surface 810 of the cap 800. The cap 800 may also have a tab 830 to facilitate its removal from a test tube 700. Although the exemplary cap 800 depicted in FIG. 8 is dimensioned to fit onto the standard test tube 700 depicted in FIG. 7, tubes and caps having other, matching, cross-sections, such as elliptical, octagonal, etc., may be used.

Having described exemplary SATs and TASes, as well as exemplary TAS holders, a method for preparing a sample aliquot using a SAT and a TAS is now described in § 4.1.3 below.

§ 4.1.3 Operation of an Exemplary SAT-TAS Combination

Figure 5A:
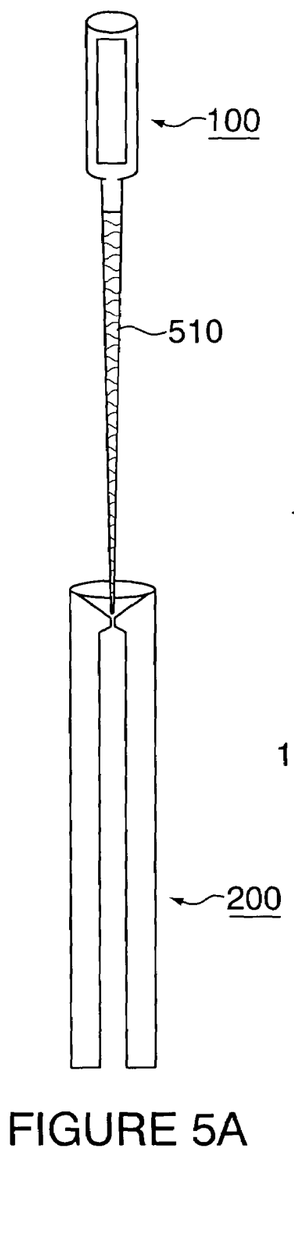
FIGS. 5*a* through 5*c* illustrate the way a fluid sample is forced from a pipette tip of a SAT to a sample aliquot cup of the SAT as the SAT is inserted into a TAS.
Figure 5B:
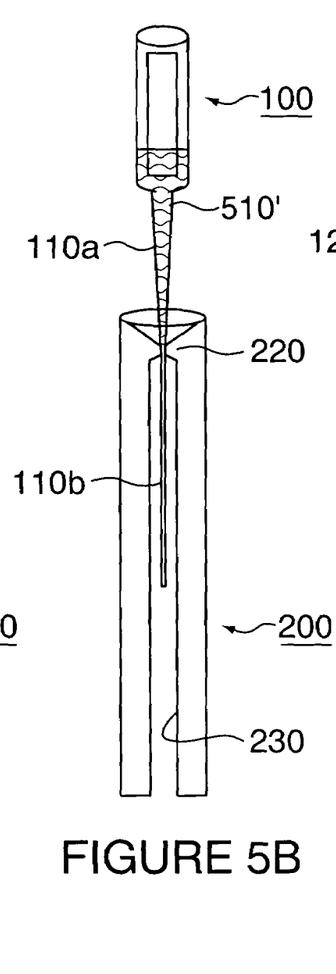
Figure 5C:
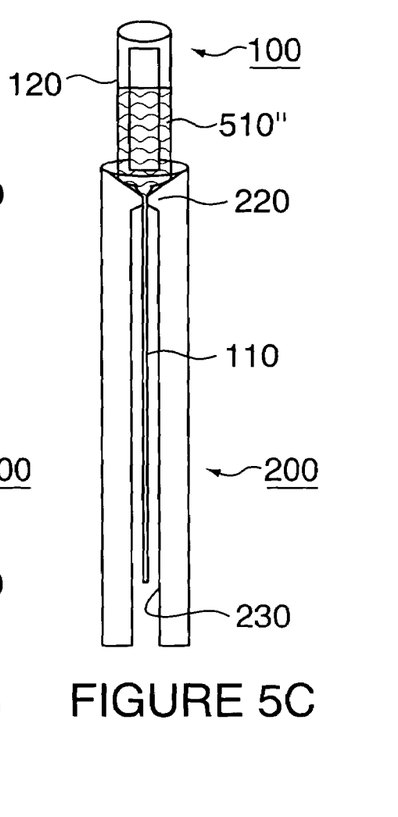

FIGS. 5a through 5c illustrate the way a fluid sample 510 is forced from a pipette tip 110 of a SAT 100 to a sample aliquot cup 120 of the SAT 100 as the SAT 100 is inserted into a TAS 200. As can be appreciated, an automated pipetting system may have been used, along with the SAT 100, to draw a fluid sample from a fluid sample source, such as a test tube for example. More specifically, the open end 122 of the aliquot cup 120 may have been fitted onto a mated fitting of an automated pipetting system. The automated pipetting system may have then positioned the pipette tip 110 of the SAT 100 such that the open end 112 of the pipette tip 110 was immersed in the sample fluid. The automated pipetting system may have then provided a vacuum to the open end 122 of the aliquot cup 120 of the SAT to draw a fluid sample into the pipette area 110. It is possible that some of the fluid sample may be held in the aliquot cup 120 of the SAT 100 at this time. However, it is expected that in most cases, the fluid sample will be held, exclusively, in the pipette tip 110 of the SAT 100 at this time. For example, referring to FIG. 5a, the fluid sample 510 is held, exclusively, in the pipette tip 110 section of the SAT.

Referring to FIG. 5b, as the SAT 100 is inserted into a TAS 200, the constricted passage 220 of the TAS 200 collapses the pipette tip 110 of the SAT 100. In this Figure, the portion of the pipette tip 110 which has been collapsed by the constricted passage 220 (that is, the portion of the pipette tip 110 below the constricted passage 220 of the TAS 200) is referred to as 110b, while the portion of the pipette tip 110 which has not yet been collapsed by the constricted passage 220 (that is, the portion of the pipette tip 110 above the constricted passage 220 of the TAS 200) is referred to as 110a. The collapsed portion of the pipette tip 10b of the SAT 100 is received by the channel 230 of the TAS 200. Notice that the fluid sample 510' remains in the portion of the SAT 100 above the constricted passage 220 of the TAS 200. Recall that the support 210 of the TAS 200 may be tapered in general or funnel shaped in particular. This taper should extend to the constricted passage 220 such that, as the SAT 100 is inserted into the TAS 200, the pipette 110 is guided, by the walls of the support 210, to the constricted passage 220.

As shown in FIG. 5c, when the SAT 100 is fully inserted into the TAS 200, the support 230 of the TAS 200 accommodates a bottom portion of the sample aliquot cup 120 of the SAT 100. Notice also that the fluid sample 510" remains in the portion of the SAT 100 above the constricted passage 220 of the TAS 200. In this example, the fluid sample 510" is held, exclusively, in the sample aliquot cup 120 section of the SAT 100. Notice also that the channel 230 of the TAS 200 is longer than the pipette tip 110 of the SAT 100. In an alternative embodiment, the channel 230 of the TAS 200 may be about the same length as the pipette tip 110 of the SAT 100.

Figure 9:
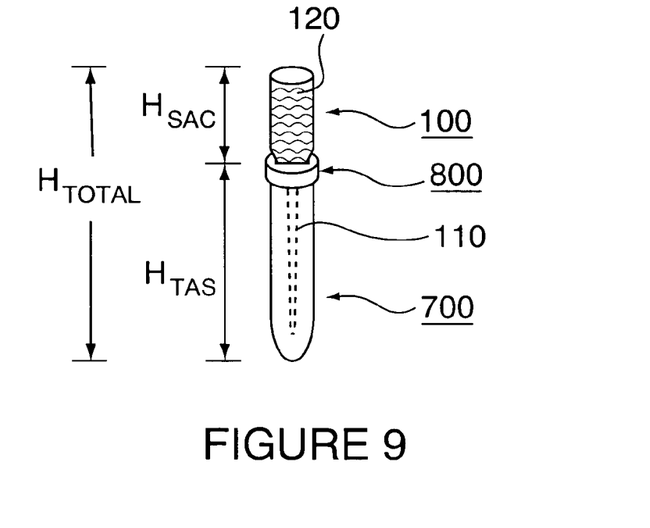
FIG. 9 is a perspective view of the SAT used with the alternative TAS.

FIG. 9 is a perspective view of the SAT 100 used with an alternative TAS defined by the tube 700 and cap 800. The height $H_{TAS}$ of the TAS is slightly greater than the height $H_{TT}$ of the test tube 700 due to the thickness of the top surface 810 of the cap 800. Thus, the height $H_{TAS}$ may be approximately 75 mm, or slightly greater. The height $H_{SAC}$ is the distance between the top of the alternative TAS and the top of the SAT 100 when the SAT 100 is fully inserted into the alternative TAS. This height $H_{SAC}$ may be 25 mm, or approximately 25 mm, for example. As shown, the sample aliquot cup 120 of the SAT 100 is held by the top surface 810 of the cap 800 and the collapsed pipette 110 is accommodated within the test tube 700. The total height of the SAT 100 fully inserted into the alternative SAT is $H_{TOTAL}$ which may be 100 mm, or approximately 100 mm, for example.

Although not shown in these Figures, the TAS 200 may be held in a TAS holder 402/404 while the SAT is being inserted.

Having described exemplary structures of the SAT and the TAS, as well as methods for using the SAT and the TAS, an automated aliquot preparation system is now described in § 4.2 below.

§ 4.2 Automated Aliquot Preparation System

This section describes an automated aliquot preparation system. First, functions which may be performed by an automated aliquot preparation system are introduced in § 4.2.1 below. Then, the structure of an exemplary automated aliquot preparation system is described in § 4.2.2 below. Finally, an operation of an exemplary automated aliquot preparation system is described in § 4.2.3 below.

§ 4.2.1 Functions of an Automated Aliquot Preparation System

The basic function of an automated aliquot preparation system is to prepare an aliquot of sample fluid from a sample fluid source. The system of the present invention uses both the SAT 100 and the TAS 200 for that purpose. An automated aliquot preparation system may also use the SAT 100 and the TAS 200 for pipetting, labeling and transporting liquid samples. The transportation of the liquid samples may rely on some means for identifying particular fluid samples.

Having described functions which may be performed by an automated aliquot preparation system, an exemplary system which may be used to perform one or more of these functions is described in § 4.2.2 below.

4.2.2 Exemplary Structures of an Automated Aliquot Preparation System

Figure 6:
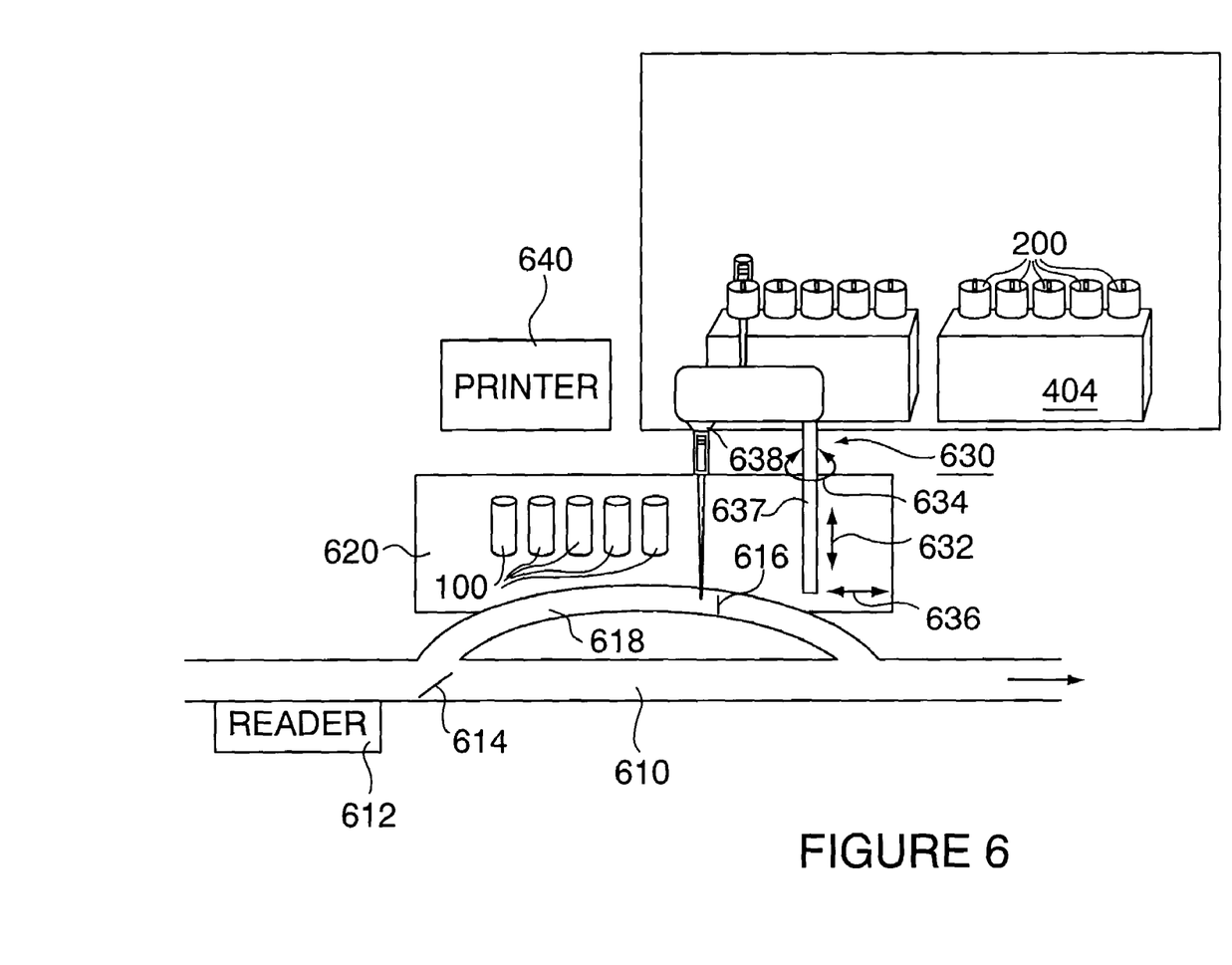
FIG. 6 illustrates an automated system which may use the SAT and TAS.

FIG. 6 illustrates an automated aliquot preparation system 600 which may use the SAT 100 and the TAS 200 described in § 4.1 above to perform one or more of the functions described in § 4.2.1 above. The automated aliquot preparation system 600 may include a system of one or more conveyers 610/618, an identification reader 612, a gate 614, a printer 640, and an automated pipetting system 630. One or more SATs 100 may be held in a rack 620. Similarly, one or more TASes 200 may be held in a rack 404.

The system of one or more conveyers may include a primary conveyer 610 and a secondary conveyer 618. The conveyers (also referred to as "sample transport lanes") may be those from Labotix, Inc. for example. The identification reader 612 may be a bar code reader, for example, and may be positioned adjacent to the primary conveyer 610 upstream of the secondary conveyer 618. The diverter gate 614 may be positioned at the upstream junction of the primary 610 and secondary 618 conveyers. The stop gate 616 may be provided on the secondary conveyer 618 so that a liquid sample source held by the stop gate 616 may be accessed by a pipette tip 110 of a SAT 100 held in the automated pipetting system 630. The automated pipetting system 630 will know where to expect the liquid sample source.

The automated pipetting 630 may be arranged such that its head fitting 638 may be positioned above the secondary conveyer 618, SATs 100 held in holder 620, and TASes 200 held in holder 404. The automated pipetter may be product number OLA6000 from Olympus Optical Co., Ltd. of Tokyo, Japan for example. The head fitting 638 may be a nipple which mates with the inside surface of the sample aliquot cup 120 of a SAT 100. Alternatively, the head fitting 638 may be any fitting which mates with the SAT 100 such that the SAT 100 is held to the head fitting 638 and such that a vacuum can be applied to the SAT 100.

The printer 640 may be positioned such that it can come into printing contact with an aliquot cup 120 of a SAT 100 held by the automated pipetter 630. The printer 640 may be a thermal printer, a laser printer, or an ink jet printer for example.

Having described the components of the automated aliquot preparation system 600 and their arrangement, an example of an operation of the automated system 600 is provided in § 4.2.3 below.

§ 4.2.3 Operation of an Exemplary Automated Pipetting System

The fluid sample sources may be test tubes for example. Carriers may be used to accommodate one or more fluid sample sources. A carrier accommodating a single fluid sample source may be referred to as a "puck-type carrier", while a carrier accommodating multiple fluid sample sources may be referred to as a "rack-type carrier". It is believed that using puck-type carriers, exclusively, will afford the greatest flexibility to the system 600. Typically, the fluid sample sources will be provided with some means of identification. Such means of identification will preferably be machine-readable, such as a bar code label for example. As the carrier carries a fluid sample source down the primary conveyer 610, a reader 612, such as a bar code reader for example, reads the means for identifying. The identification read by the reader 612 is interpreted by a controller (not shown), such as a computer for example, which controls the gate 614 based on the read means for identifying. More specifically, if an aliquot is to be drawn from the fluid sample source, the controller controls the gate 614 to divert the carrier carrying the fluid sample source to the secondary conveyer 618. The controller may compare the read identification with a list of identifications assigned to the automated pipetting system 630 station.

On the secondary conveyer 618, the carrier is stopped by the stop gate 616. Alternatively, or in addition, the secondary conveyer 618 may stop once the carrier is properly positioned with respect to the automated pipetting system 630. Such positioning may be effected in a number of other known ways. Thus, in one embodiment of the system 600, the secondary conveyer 618 may be controlled independently of primary conveyer 610.

At this point, the head fitting 638 of the automated pipetting system 630 may have already been fitted with a SAT 100. A base 620 may hold one or more SATs 100. The head fitting 638 of the automated pipetting system 630 may be moved vertically, as shown by arrows 632, with respect to the secondary conveyer 618, laterally, as shown by arrows 636, with respect to the secondary conveyer 618, and/or radially, as shown by arrows 634, with respect to shaft 637. Although not shown, the head fitting 638 of the automated pipetting system 630 may also be moved longitudinally with respect to the secondary conveyer 618.

In any event, the pipette tip 110 of the SAT 100 held by the automated pipetting system 630 is positioned over the fluid sample source and lowered into the fluid sample. A sample is then drawn, via the opening 112 at the end of the pipette tip 110, into the SAT 100. The SAT 100 is then raised from the fluid sample source and positioned above an empty TAS 200, such as a TAS 200 held in rack 404. The automated pipetting system 630 then lowers the SAT 100 into the TAS 200. As described in section 4.1.3 above with reference to FIGS. 5a through 5c, as the SAT 100 is inserted into the TAS 200, the pipette tip 110 is collapsed by the constricted passage 220, thereby forcing the fluid sample upward into the sample aliquot cup 120 of the SAT 100. The automated pipetting system 630 then releases the SAT 100.

At some point, the printer 640 prints another means for identification, such as a bar code for example, onto the SAT 100. In one embodiment, the printer 640 prints the same bar code as the one provided on the fluid sample source, onto the sample aliquot cup 120 of the SAT 100. This printing may be done (a) before the SAT 100 is fit onto the head fitting 638 of the automated pipetting system 630, (b) after the SAT 100 is fit onto the head fitting 638 of the automated pipetting system 630 but before the fluid sample is drawn, (c) after the fluid sample is drawn but before the SAT 100 is inserted into the TAS 200, or (d) after the SAT 100 is inserted into the TAS 200. In one alternative embodiment, the bar code of the fluid sample source may be re-scanned at the stop gate 616 and the printer 640 can duplicate the bar code onto the SAT 100.

Once fluid is drawn from the fluid sample source, the stop gate 616 may open and/or the secondary conveyer 618 may restart such that the fluid sample source will return to the primary conveyer 610. In this way, any fluid remaining may be used by downstream testing stations (e.g., an immunoassay analyzer). As can be appreciated, such a dual lane (that is, primary and secondary) conveyance system is useful since puck-carriers can be diverted into the local (that is, secondary) lane for each station while the by-pass (that is, primary) lane conveys samples to other destinations. In this way, various types of fluid sample sources (e.g., purple, blue, and green top tubes, and urine samples) can be routed on the same conveyer to the appropriate instrument stations.

§ 4.3 CONCLUSIONS

Thus, the present invention provides a system 600 for preparing aliquots of sample fluids which is more efficient, both in the economy of motion and in the materials used, than known systems.

What is claimed is:

1. An apparatus for preparing a fluid sample, the apparatus comprising:
   a) a first part including
      i) a pipette tip having an open tip end, and
      ii) a sample cup, fluidly coupled with the pipette tip and having an open end; and
   b) a second part including
      i) a channel for receiving the pipette tip of the first part,
      ii) a support for accommodating at least a portion of the sample cup of the first part, and
      iii) a constricted passage, arranged between the channel and the support, for collapsing the pipette tip of the first part as the first part is inserted into the second part, wherein the pipette tip of the first part and the constricted passage of the second part are designed such that, as the pipette tip passes through the constricted passage, walls defining the pipette tip collapse inwardly and form a liquid seal.

2. An apparatus for preparing a fluid sample, the apparatus comprising:
   a) a first part including
      i) a pipette tip having an open tip end, and
      ii) a sample cup, fluidly coupled with the pipette tip and having an open end; and
   b) a second part including
      i) a channel for receiving the pipette tip of the first part,
      ii) a support for accommodating at least a portion of the sample cup of the first part, and
      iii) a constricted passage, arranged between the channel and the support, for collapsing the pipette tip of the first part as the first part is inserted into the second part, wherein the support of the second part is shaped as a funnel.

3. An apparatus for preparing a fluid sample, the apparatus comprising:
   a) a first part including
      i) a pipette tip having an open tip end, and
      ii) a sample cup, fluidly coupled with the pipette tip and having an open end; and
   b) a second part including
      i) a channel for receiving the pipette tip of the first part,
      ii) a support for accommodating at least a portion of the sample cup of the first part, and
      iii) a constricted passage, arranged between the channel and the support, for collapsing the pipette tip of the first part as the first part is inserted into the second part, wherein the support of the second part is tapered.

4. An apparatus for preparing a fluid sample, the apparatus comprising:
   a) a first part including
      i) a pipette tip having an open tip end, and
      ii) a sample cup, fluidly coupled with the pipette tip and having an open end; and
   b) a second part including
      i) a channel for receiving the pipette tip of the first part,
      ii) a support for accommodating at least a portion of the sample cup of the first part, and iii) a constricted passage, arranged between the channel and the support, for collapsing the pipette tip of the first part as the first part is inserted into the second part, wherein the pipette tip is tapered.

5. The apparatus of claim 4 wherein the pipette tip is formed of a collapsible material.

6. The apparatus of claim 4 wherein the pipette tip is formed of a flexible and collapsible material.

7. The apparatus of claim 4 wherein a length of the channel of the second part is at least as long as a length of the pipette tip of the first part.

8. The apparatus of claim 4 wherein the open end of the sample cup of the first part is dimensioned to mate with an automated pipetting system.

9. The apparatus of claim 4 wherein the support of the second part is shaped to match a bottom of the sample cup of the first part.

10. The apparatus of claim 4 wherein the support of the second part is shaped to guide the pipette tip of the first part to the constricted passage of the second part as the first part is inserted into the second part.

11. The apparatus of claim 4 wherein the pipette tip of the first part and the constricted passage of the second part are designed such that, as the pipette tip passes through the constricted passage, walls defining the pipette tip collapse inwardly and form a liquid seal such that liquid in the pipette tip of the first part is forced upward into the sample cup of the first part.

12. The apparatus of claim 4 wherein the pipette tip of the first part and the constricted passage of the second part are designed such that, as the pipette tip passes through the constricted passage, walls defining the pipette tip collapse inwardly and form a moving liquid seal such that the moving liquid seal progresses up the pipette tip as the pipette tip passes through the constricted passage.

13. The apparatus of claim 4 wherein the pipette tip of the first part and the constricted passage of the second part are designed such that, as the pipette tip passes through the constricted passage, walls defining the pipette tip collapse inwardly and form a moving liquid seal such that the moving liquid seal progresses up the pipette tip as the pipette tip passes through the constricted passage, wherein the moving liquid seal forces liquid in the pipette tip upward into the sample cup.

14. An apparatus for preparing a fluid sample, the apparatus comprising:
a) a first part including
i) a pipette tip having an open tip end, and
ii) a sample cup, fluidly coupled with the pipette tip and having an open end; and
b) a second part including
i) a channel for receiving the pipette tip of the first part,
ii) a support for accommodating at least a portion of the sample cup of the first part, and
iii) a constricted passage, arranged between the channel and the support, for collapsing the pipette tip of the first part as the first part is inserted into the second part, wherein the constricted passage has a fixed cross section.

15. The apparatus of claim 14 wherein the pipette tip of the first part and the constricted passage of the second part are designed such that, as the pipette tip passes through the constricted passage, walls defining the pipette tip collapse inwardly and form a liquid seal such that liquid in the pipette tip of the first part is forced upward into the sample cup of the first part.

16. The apparatus of claim 14 wherein the pipette tip of the first part and the constricted passage of the second part are designed such that, as the pipette tip passes through the constricted passage, walls defining the pipette tip collapse inwardly and form a moving liquid seal such that the moving liquid seal progresses up the pipette tip as the pipette tip passes through the constricted passage.

17. The apparatus of claim 14 wherein the pipette tip of the first part and the constricted passage of the second part are designed such that, as the pipette tip passes through the constricted passage, walls defining the pipette tip collapse inwardly and form a moving liquid seal such that the moving liquid seal progresses up the pipette tip as the pipette tip passes through the constricted passage, wherein the moving liquid seal forces liquid in the pipette tip upward into the sample cup.

18. The apparatus of claim 14 wherein the pipette tip is formed of a collapsible material.

19. The apparatus of claim 14 wherein the pipette tip is formed of a flexible and collapsible material.

20. The apparatus of claim 14 wherein a length of the channel of the second part is at least as long as a length of the pipette tip of the first part.

21. The apparatus of claim 14 wherein the open end of the sample cup of the first part is dimensioned to mate with an automated pipetting system.

22. The apparatus of claim 14 wherein the support of the second part is shaped to match a bottom of the sample cup of the first part.

23. The apparatus of claim 14 wherein the support of the second part is shaped to guide the pipette tip of the first part to the constricted passage of the second part as the first part is inserted into the second part.

24. An apparatus for preparing a fluid sample, the apparatus comprising:
a) a first part including
i) a pipette tip having an open tip end, and
ii) a sample cup, fluidly coupled with the pipette tip and having an open end; and
b) a second part including
i) a channel for receiving the pipette tip of the first part,
ii) a support for accommodating at least a portion of the sample cup of the first part, and
iii) a constricted passage, arranged between the channel and the support, for collapsing the pipette tip of the first part as the first part is inserted into the second part, wherein the pipette tip of the first part and the constricted passage of the second part are designed such that, as the pipette tip passes through the constricted passage, walls defining the pipette tip collapse inwardly and form a liquid seal such that liquid in the pipette tip of the first part is forced upward into the sample cup of the first part.

25. An apparatus for preparing a fluid sample, the apparatus comprising:
a) a first part including
i) a pipette tip having an open tip end, and
ii) a sample cup, fluidly coupled with the pipette tip and having an open end; and
b) a second part including
i) a channel for receiving the pipette tip of the first part,
ii) a support for accommodating at least a portion of the sample cup of the first part, and iii) a constricted passage, arranged between the channel and the support, for collapsing the pipette tip of the first part as the first part is inserted into the second part, wherein the pipette tip of the first part and the constricted passage of the second part are designed such that, as the pipette tip passes through the constricted passage, walls defining the pipette tip collapse inwardly and form a moving liquid seal such that the moving liquid seal progresses up the pipette tip as the pipette tip passes through the constricted passage.

26. An apparatus for preparing a fluid sample, the apparatus comprising:
   a) a first part including
      i) a pipette tip having an open tip end, and
      ii) a sample cup, fluidly coupled with the pipette tip and having an open end; and
   b) a second part including
      i) a channel for receiving the pipette tip of the first part,
      ii) a support for accommodating at least a portion of the sample cup of the first part, and
      iii) a constricted passage, arranged between the channel and the support, for collapsing the pipette tip of the first part as the first part is inserted into the second part, wherein the pipette tip of the first part and the constricted passage of the second part are designed such that, as the pipette tip passes through the constricted passage, walls defining the pipette tip collapse inwardly and form a moving liquid seal such that the moving liquid seal progresses up the pipette tip as the pipette tip passes through the constricted passage, wherein the moving liquid seal forces liquid in the pipette tip upward into the sample cup.

* * * * *